United States Patent
Zhao

(10) Patent No.: US 7,625,898 B2
(45) Date of Patent: Dec. 1, 2009

(54) POSACONAZOLE POLYMER CONJUGATES AND METHODS OF TREATMENT USING POSACONAZOLE AND POLYMER CONJUGATES THEREOF

(75) Inventor: Hong Zhao, Edison, NJ (US)

(73) Assignee: Enzon Pharmaceuticals, Inc., Bridgewater, NJ (US)

(*) Notice: Subject to any disclaimer, the term of this patent is extended or adjusted under 35 U.S.C. 154(b) by 0 days.

(21) Appl. No.: 12/014,391

(22) Filed: Jan. 15, 2008

(65) Prior Publication Data

US 2008/0171013 A1 Jul. 17, 2008

Related U.S. Application Data

(60) Provisional application No. 60/885,089, filed on Jan. 16, 2007.

(51) Int. Cl.
*A01N 43/58* (2006.01)
(52) U.S. Cl. .................. 514/247; 424/400; 514/772
(58) Field of Classification Search .................. None
See application file for complete search history.

(56) References Cited

U.S. PATENT DOCUMENTS

| | | | |
|---|---|---|---|
| 5,643,575 A | 7/1997 | Martinez et al. | |
| 5,661,151 A | 8/1997 | Saksena et al. | |
| 5,919,455 A | 7/1999 | Greenwald et al. | |
| 5,965,566 A | 10/1999 | Greenwald et al. | |
| 6,113,906 A | 9/2000 | Greenwald et al. | |
| 6,153,655 A | 11/2000 | Martinez et al. | |
| 6,566,506 B2 | 5/2003 | Greenwald et al. | |
| 6,756,037 B2 | 6/2004 | Greenwald et al. | |
| 2007/0049726 A1 | 3/2007 | Zhao et al. | |
| 2007/0078219 A1 | 4/2007 | Zhao et al. | |

FOREIGN PATENT DOCUMENTS

WO 2005000208 A2 1/2005

OTHER PUBLICATIONS

International Search Report and Written Opinion dated Jul. 21, 2008 issued in PCT/US08/51075.
Package Insert of Posaconazole.
Shearwater Corporation's catalog, Polyethlene Glycol and Derivatices for Biomedical Application, 2001.
NOF Corp. Drug Delivery System catalog, Ver.8, Apr. 2006.

*Primary Examiner*—Eric E. Silverman
(74) *Attorney, Agent, or Firm*—Lucas & Mercanti, LLP

(57) ABSTRACT

Improved posaconazole-based compositions and methods of treating and preventing fungal infections, cancer or metastatic diseases are disclosed. In preferred aspects, the conjugates are PEG-posaconazole conjugates in which the PEG has a molecular weight of about 20,000 daltons.

10 Claims, 1 Drawing Sheet

HNPEGNH=NH-(CH₂CH₂O)ₙ-CH₂CH₂NH

POSACONAZOLE POLYMER CONJUGATES AND METHODS OF TREATMENT USING POSACONAZOLE AND POLYMER CONJUGATES THEREOF

CROSS-REFERENCE TO RELATED APPLICATION

This application claims the benefit of priority from U.S. Provisional Patent Application Ser. No. 60/885,089 filed Jan. 16, 2007, the contents of which are incorporated herein by reference.

FIELD OF THE INVENTION

The present invention relates to posaconazole-polymer conjugates having improved antifungal activity. The invention further relates to the use of posaconazole and polymeric conjugates including the same in the treatment of cancer and metastatic diseases.

BACKGROUND OF THE INVENTION

U.S. Pat. No. 5,661,151 discloses posaconazole and its use as antifungal agent with a broad spectrum of activity. In vitro and in vivo studies demonstrated that posaconazole has good activity against Candida species (including albicans, glabrata, and tropicalis), as well as other opportunistic fungi, including but not limited to, Aspergillus, Fusarium, Basidiomycetes, Blastomyces, Coccidioides, Histoplasma, Zygomycetes, and Scedosporium, and opportunistic moniliaceous and dematiaceous molds and dermatophyte. Posaconazole, however, is very insoluble, (water solubility <0.002 mg/mL). Therefore, it has been a challenge to provide intravenous or parenteral formulations having desirable pharmacologic properties.

Commonly-assigned U.S. Pat. No. 5,965,566 discloses releasable PEG conjugates of various anticancer agents using ester-based linkages. The prodrug conjugates are designed with various bifunctional spacers inserted between the PEG and parent compound to be released. These bifunctional spacers are believed to play a role in the modulation of the hydrolysis reaction which frees the parent compound in vivo. In certain examples, a diglycolic-acid based spacer is used. Details are described in FIG. 2 therein. The contents of the '566 patent are incorporated herein by reference.

In spite of the prior work in this regard, there continues to be a need for improved posaconazole compositions and methods of treatment using the same. The present invention addresses these needs.

SUMMARY OF THE INVENTION

In one aspect of the invention, there are provided improved polymeric conjugates containing posaconazole and a substantially non-antigenic polymer. The substantially non-antigenic polymer is preferably a polyalkylene oxide such as polyethylene glycol.

In one preferred aspect of the invention, the polymeric conjugates of the invention have Formula (I):

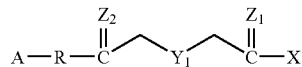

wherein
A is a capping group or

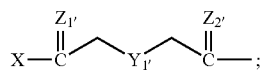

X is

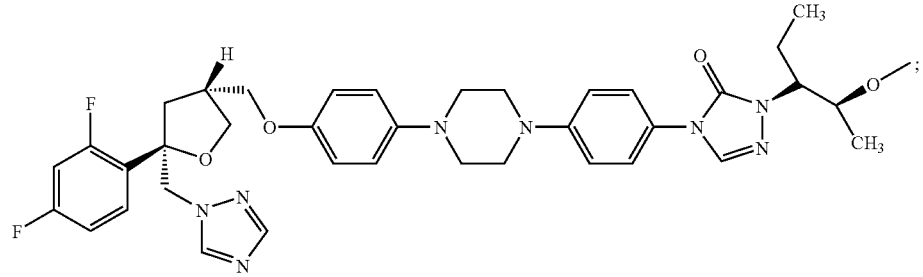

$Z_1$, $Z_{1'}$, $Z_2$ and $Z_{2'}$ are independently selected from among O, S and $NR_i$;

R is a polyalkylene oxide;

$Y_1$ and $Y_{1'}$ are independently O, S, SO, $SO_2$, $CR_2R_3$ or $NR_4$; and $R_1$, $R_2$, $R_3$ and $R_4$ are independently selected from among hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy.

In one preferred embodiment, the polymeric conjugates of the invention have Formula (II):

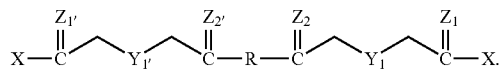

In another aspect of the invention, there are provided methods of treating and/or preventing fungal infections in a mammal. The methods include administering an anti-fungally effective amount of the polymeric conjugates described herein to the mammal.

Further aspects of the invention provide methods of treating and/or preventing cancer or metastatic diseases in a mammal. These methods include administering to the mammal, preferably human, an effective amount of posaconazole or, if desired, any one of a wide number of suitable polymeric conjugates, including those described herein or those polymeric conjugates containing posaconazole described previously.

The posaconazole or polymeric conjugates containing the same are preferably administered parenterally, i.e. intravenously or intramuscularly or subcutaneously.

Some of the advantages associated with some preferred polymer conjugates described herein include the fact that water solubility is significantly increased as compared to the unmodified form. Thus, intravenous dosing is possible. Moreover, the potency of the some preferred polymer conjugates unexpectedly higher against certain fungal strains. This allows the drug to be used in lower doses and/or in the treatment of fungal infections which might not otherwise be candidates for treatment with posaconazole. Other and further advantages, including those associated with using posaconazole in methods of treating or reducing metastatic diseases, tumors, cancers, etc. will be apparent to those of ordinary skill in the field upon reading the specification provided herein.

For purposes of the present invention, the term "residue" shall be understood to mean that portion of a compound, to which it refers, i.e. PEG, etc. that remains after it has undergone a substitution reaction with another compound.

For purposes of the present invention, the term "polymeric residue" or "PEG residue" shall each be understood to mean that portion of the polymer or PEG which remains after it has undergone a reaction with other compounds, moieties, etc.

For purposes of the present invention, the term "alkyl" as used herein refers to a saturated aliphatic hydrocarbon, including straight-chain, branched-chain, and cyclic alkyl groups. The term "alkyl" also includes alkyl-thio-alkyl, alkoxyalkyl, cycloalkylalkyl, heterocycloalkyl, $C_{1-6}$ hydrocarbonyl, groups. Preferably, the alkyl group has 1 to 12 carbons. More preferably, it is a lower alkyl of from about 1 to 7 carbons, yet more preferably about 1 to 4 carbons. The alkyl group can be substituted or unsubstituted. When substituted, the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, heteroaryl, alkenyl, alkynyl, $C_{1-6}$ hydrocarbonyl, aryl, and amino groups.

For purposes of the present invention, the term "substituted" as used herein refers to adding or replacing one or more atoms contained within a functional group or compound with one of the moieties from the group of halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups.

The term "alkenyl" as used herein refers to groups containing at least one carbon-carbon double bond, including straight-chain, branched-chain, and cyclic groups Preferably, the alkenyl group has about 2 to 12 carbons. More preferably, it is a lower alkenyl of from about 2 to 7 carbons, yet more preferably about 2 to 4 carbons. The alkenyl group can be substituted or unsubstituted. When substituted the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups.

The term "alkynyl" as used herein refers to groups containing at least one carbon-carbon triple bond, including straight-chain, branched-chain, and cyclic groups. Preferably, the alkynyl group has about 2 to 12 carbons. More preferably, it is a lower alkynyl of from about 2 to 7 carbons, yet more preferably about 2 to 4 carbons. The alkynyl group can be substituted or unsubstituted. When substituted the substituted group(s) preferably include halo, oxy, azido, nitro, cyano, alkyl, alkoxy, alkyl-thio, alkyl-thio-alkyl, alkoxyalkyl, alkylamino, trihalomethyl, hydroxyl, mercapto, hydroxy, cyano, alkylsilyl, cycloalkyl, cycloalkylalkyl, heterocycloalkyl, heteroaryl, alkenyl, alkynyl, $C_{1-6}$ hydrocarbonyl, aryl, and amino groups. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkyl" as used herein refers to a $C_{3-8}$ cyclic hydrocarbon. Examples of cycloalkyl include cyclopropyl, cyclobutyl, cyclopentyl, cyclohexyl, cycloheptyl and cyclooctyl.

The term "cycloalkenyl" as used herein refers to a $C_{3-8}$ cyclic hydrocarbon containing at least one carbon-carbon double bond. Examples of cycloalkenyl include cyclopentenyl, cyclopentadienyl, cyclohexenyl, 1,3-cyclohexadienyl, cycloheptenyl, cycloheptatrienyl, and cyclooctenyl.

The term "cycloalkylalkyl" as used herein refers to an alkyl group substituted with a $C_{3-8}$ cycloalkyl group. Examples of cycloalkylalkyl groups include cyclopropylmethyl and cyclopentylethyl.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

An "alkylaryl" group as used herein refers to an aryl group substituted with an alkyl group.

An "aralkyl" group as used herein refers to an alkyl group substituted with an aryl group.

The term "alkoxyalkyl" group as used herein refers to an alkyl group substituted with an alkloxy group.

The term "alkyl-5-alkyl" as used herein refers to an alkyl-5-alkyl thioether, for example methylthiomethyl or methylthioethyl.

The term "amino" as used herein refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The term "alkylcarbonyl" as used herein refers to a carbonyl group substituted with alkyl group.

The terms "halogen" or "halo" as used herein refer to fluorine, chlorine, bromine, and iodine.

The term "heterocycloalkyl" as used herein refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrrolidinyl.

The term "heteroaryl" as used herein refers to an aromatic ring system containing at least one heteroatom selected from nitrogen, oxygen, and sulfur. The heteroaryl ring can be fused or otherwise attached to one or more heteroaryl rings, aromatic or non-aromatic hydrocarbon rings or heterocycloalkyl rings. Examples of heteroaryl groups include, for example, For purposes of the present invention, the term "linked" shall be understood to include covalent (preferably) or non-covalent attachment of one group to another, i.e., as a result of a chemical reaction.

The terms "effective amounts" and "sufficient amounts" for purposes of the present invention shall mean an amount which achieves a desired effect or therapeutic effect as such effect is understood by those of ordinary skill in the art.

DETAILED DESCRIPTION OF THE INVENTION

1. Posaconazole

Figure 1:
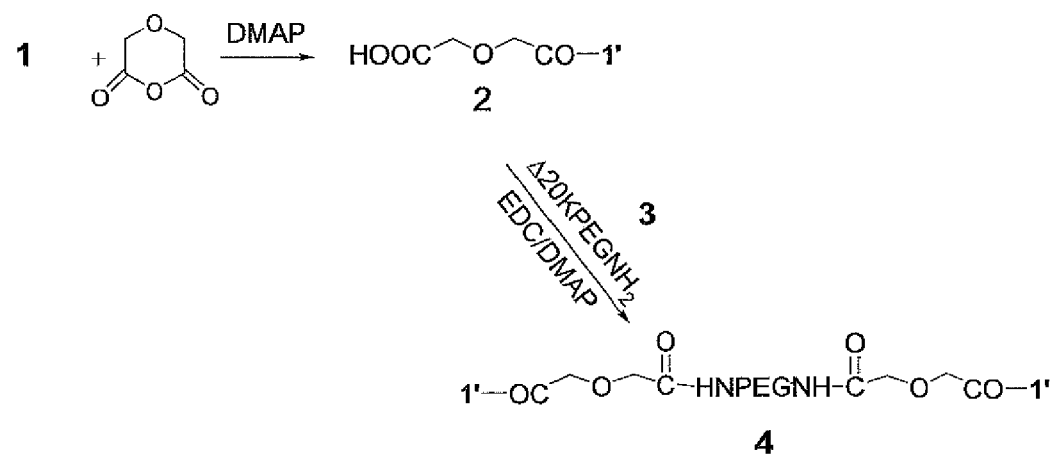
FIG. 1 provides a reaction scheme corresponding to Examples 1-2.
Figure 1:
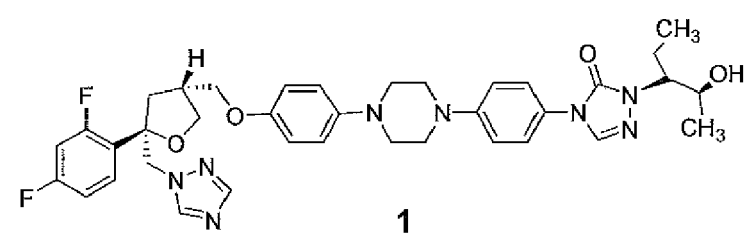
Figure 1:
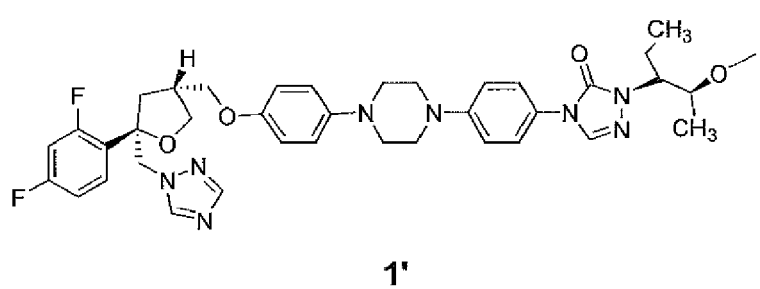

Preferred aspects of the invention include the posaconazole or pharmaceutically acceptable salts thereof. U.S. Pat. No. 5,661,151, the contents of which are incorporated herein by reference, describes posaconazole, i.e.

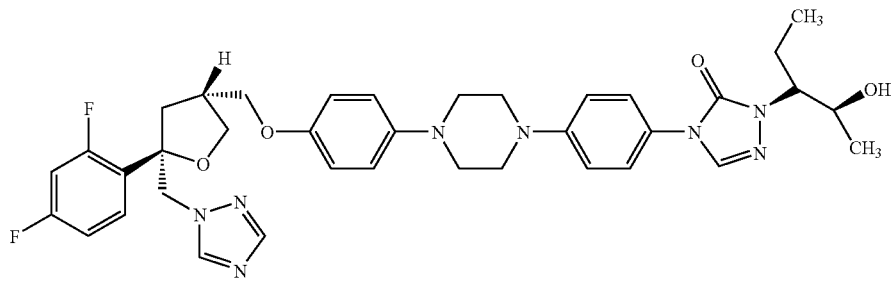

pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "heteroatom" as used herein refers to nitrogen, oxygen, and sulfur.

In some embodiments, substituted alkyls include carboxyalkyls, aminoalkyls, dialkylaminos, hydroxyalkyls and mercaptoalkyls; substituted alkenyls include carboxyalkenyls, aminoalkenyls, dialkenylaminos, hydroxyalkenyls and mercaptoalkenyls; substituted alkynyls include carboxyalkynyls, aminoalkynyls, dialkynylaminos, hydroxyalkynyls and mercaptoalkynyls; substituted cycloalkyls include moieties such as 4-chlorocyclohexyl; aryls include moieties such as napthyl; substituted aryls include moieties such as 3-bromo phenyl; aralkyls include moieties such as tolyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo shall be understood to include fluoro, chloro, iodo and bromo.

For purposes of the present invention, "positive integer" shall be understood to include an integer equal to or greater than 1 and as will be understood by those of ordinary skill to be within the realm of reasonableness by the artisan of ordinary skill.

and related compounds. For purposes of the present invention, it will be understood that when "posaconazole" is used, it is to be understood as representing a preferred embodiment of the invention. Alternative embodiments of the invention include related triazoles having primarily, but not exclusively, anti-fungal activity.

For purposes of the present invention, "anti-fungal activity" shall be understood mean that the compounds and compositions of the present invention are capable of treating, reducing or otherwise resolving fungal infections, including but not limited to, candidiasis, aspergillosis, cryptococcosis and funsariosis as well as fungal infection due to Blasidiomycetes, Blastomyces, Coccidioides, Histoplasma, Zygomycetes, Microsporum, Trichophyton, Scedosporium, and the like.

For purposes of the present invention, treatment of "cancer", "metastatic disease" "tumor", etc. shall be understood to include methods for treating cancers, whether solid or hematopoietic. Examples of cancers include head, neck, breast brain, breast lung, such as non-small cell lung, ovarian, pancreatic, prostate, renal, colorectal, cervical, acute leukemia, and gastric cancer, lymphomas, etc., to name but a few.

2. Substantially Non-Antigenic Polymers

The substantially non-antigenic polymers which can be used in various aspects of the invention include any of those known to those of ordinary skill which are capable of covalently attaching to the posaconazole or related triazole in a way which allows the biologic activity to be retained either while attached to the polymer or upon release if the polymer is included as part of a prodrug system. Suitable polymers include those available from Enzon Pharmaceuticals, Nektar or other known suppliers of activated PEG's.

The polymeric substances included herein are preferably water-soluble at room temperature. A non-limiting list of such polymers include polyalkylene oxide (PAO) homopolymers such as polyethylene glycol (PEG) or polypropylene glycols, polyoxyethylenated polyols, copolymers thereof and block copolymers thereof provided that the water solubility of the block copolymers is maintained.

The polyalkylene oxide has an average molecular weight from about 1,000 to about 100,000 daltons, preferably from about 5,000 to about 60,000 daltons. The polyalkylene oxide can be more preferably from about 12,000 to about 24,000. In one particular embodiment, polymeric portion has a molecular weight of about 20,000 daltons. The polymers described herein include a linear, branched or multi-armed polyalkylene oxide.

Preferably, the polyalkylene oxide includes polyethylene glycol (PEG). PEG is generally represented by the structure:

$$-O-(CH_2CH_2O)_n-$$

where (n) represents the degree of polymerization for the polymer, and is dependent on the molecular weight of the polymer. The polyethylene glycol (PEG) residue portion of the invention can be also represented by the structure $$-Y_{11}-(CH_2CH_2O)_n-CH_2CH_2Y_{11'}-,$$

wherein:

$Y_{11}$ and $Y_{11'}$ are independently O, S, or $NR_{11}$;

$R_{11}$ is selected from among hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

(n) is an integer from about 10 to about 2300.

Some linear PEG's useful for linking the posaconazole either directly or in combination with a bifunctional spacer, include:

$$CH_3-O-(CH_2CH_2O)_n-CH_2CH_2O-,$$

$$CH_3-O-(CH_2CH_2O)_n-CH_2CH_2NH-,$$

$$CH_3-O-(CH_2CH_2O)_n-CH_2CH_2S-,$$

$$-O-(CH_2CH_2O)_n-CH_2CH_2O-,$$

$$-NH-(CH_2CH_2O)_n-CH_2CH_2NH-, \text{ and}$$

$$-S-(C_2CH_2O)_n-CH_2CH_2S-$$

where (n) is a positive integer, preferably selected so that the average molecular weight is from about 1,000 to about 100,000, preferably from about 5,000 to about 60,000 and more preferably from about 12,000 to about 24,000. Other molecular weights are also contemplated so as to accommodate the needs of the artisan. The degree of polymerization for the polymer represents the number of repeating units in the polymer chain and is dependent on the molecular weight of the polymer. In those preferred aspects of the invention where bis-polymers, bis-PEG, are desired, the terminal methyl group is replaced with the same terminal group found on the opposite end.

In alternative aspects, the posaconazole polymer conjugates are prepared using branched polymer residues (i.e. U-PEG) such as those described commonly assigned U.S. Pat. Nos. 5,643,575, 5,919,455, 6,113,906 and 6,566,506, the disclosure of each being incorporated herein by reference. A non-limiting list of such polymers corresponds to polymer systems (i)-(iv) with the following structures:

(i)

$$\begin{array}{c} mPEG-O-\overset{O}{\underset{}{C}}-\underset{H}{N}\diagdown \underset{}{CH_2} \\ \phantom{mPEG-O-C-N} \diagdown \underset{}{CH}-Y_{61}-, \\ mPEG-O-\overset{O}{\underset{}{C}}-\underset{H}{N}\diagup \underset{}{CH_2} \end{array}$$

(ii)

$$\begin{array}{c} m\text{-}PEG-\overset{H}{N}-\overset{O}{\underset{}{C}}\diagdown \\ \phantom{m\text{-}PEG-N-C} (CH_2)_{w62} \\ \phantom{m\text{-}PEG-N-C} | \\ \phantom{m\text{-}PEG-N-C} N- \\ \phantom{m\text{-}PEG-N-C} | \\ \phantom{m\text{-}PEG-N-C} (CH_2)_{w63}, \\ m\text{-}PEG-\overset{H}{N}-\overset{}{\underset{O}{C}}\diagup \end{array}$$

(iii)

$$\begin{array}{c} m\text{-}PEG-O-\overset{O}{\underset{}{C}}-\underset{}{\overset{H}{N}}\diagdown \\ \phantom{m\text{-}PEG-O-C-N} (CH_2)_4 \\ \phantom{m\text{-}PEG-O-C-N} | \\ \phantom{m\text{-}PEG-O-C-N} CH-Y_{61}- \text{ and} \\ m\text{-}PEG-O-\overset{}{\underset{O}{C}}-\underset{H}{N}\diagup \end{array}$$

(iv)

$$\begin{array}{c} m\text{-}PEG-O-\overset{O}{\underset{}{C}}-NH\diagdown \\ \phantom{m\text{-}PEG-O-C-NH} (CH_2)_{w62} \\ \phantom{m\text{-}PEG-O-C-NH} | \\ \phantom{m\text{-}PEG-O-C-NH} N- \\ \phantom{m\text{-}PEG-O-C-NH} | \\ \phantom{m\text{-}PEG-O-C-NH} (CH_2)_{w63} \\ m\text{-}PEG-O-\overset{}{\underset{O}{C}}-\underset{H}{N}\diagup \end{array}$$

wherein:

$Y_{61}$ is O, S or $NR_{61}$;

(w62) and (w63) are independently a positive integer, preferably from about 1 to about 10, more preferably from about 1 to about 4;

mPEG is methoxy PEG wherein PEG is previously defined and a total molecular weight of the polymer portion is from about 1,000 to about 100,000 daltons; and $R_{61}$ is selected from among hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy.

Also useful are polypropylene glycols, "star-PEG's" and multi-armed PEG's such as those described in Shearwater (now Nektar) Corporation's 2001 catalog "Polyethylene Glycol and Derivatives for Biomedical Application". See also "star-PEG" or multi-armed PEG's such as those described in NOF Corp. Drug Delivery System catalog, Ver. 8, April 2006.

The disclosure of each of the foregoing is incorporated herein by reference. Specially, the PEG can be of the formula:

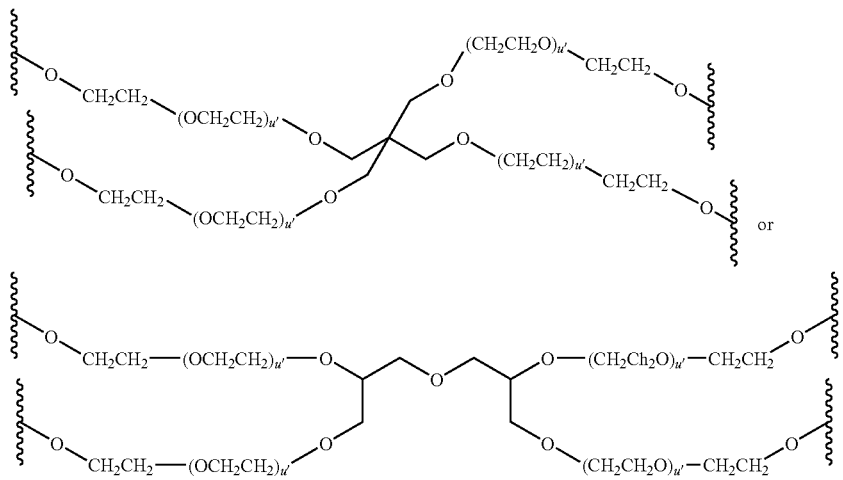

wherein:

(u') is an integer from about 4 to about 455, to preferably provide polymers having a total molecular weight of from about 5,000 to about 60,000; and up to 3 terminal portions of the residue is/are capped with a methyl or other lower alkyl. The remaining terminal(s) are functionalized for attachment of a bifunctional linker and posaconazole. It will be understood that the water-soluble polymer can be functionalized for attachment to the bifunctional linkage groups if required without undue experimentation.

In some preferred embodiments, all 4 of the PEG arms can be converted to suitable activating groups, for facilitating attachment to a bifunctional linker and posaconazonle. Such compounds prior to conversion include:

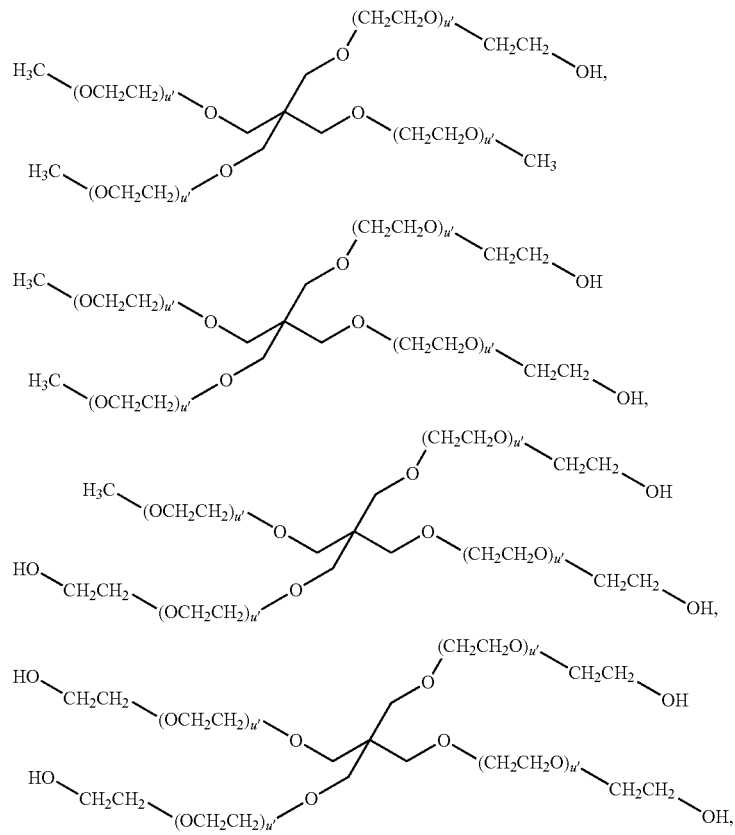

-continued

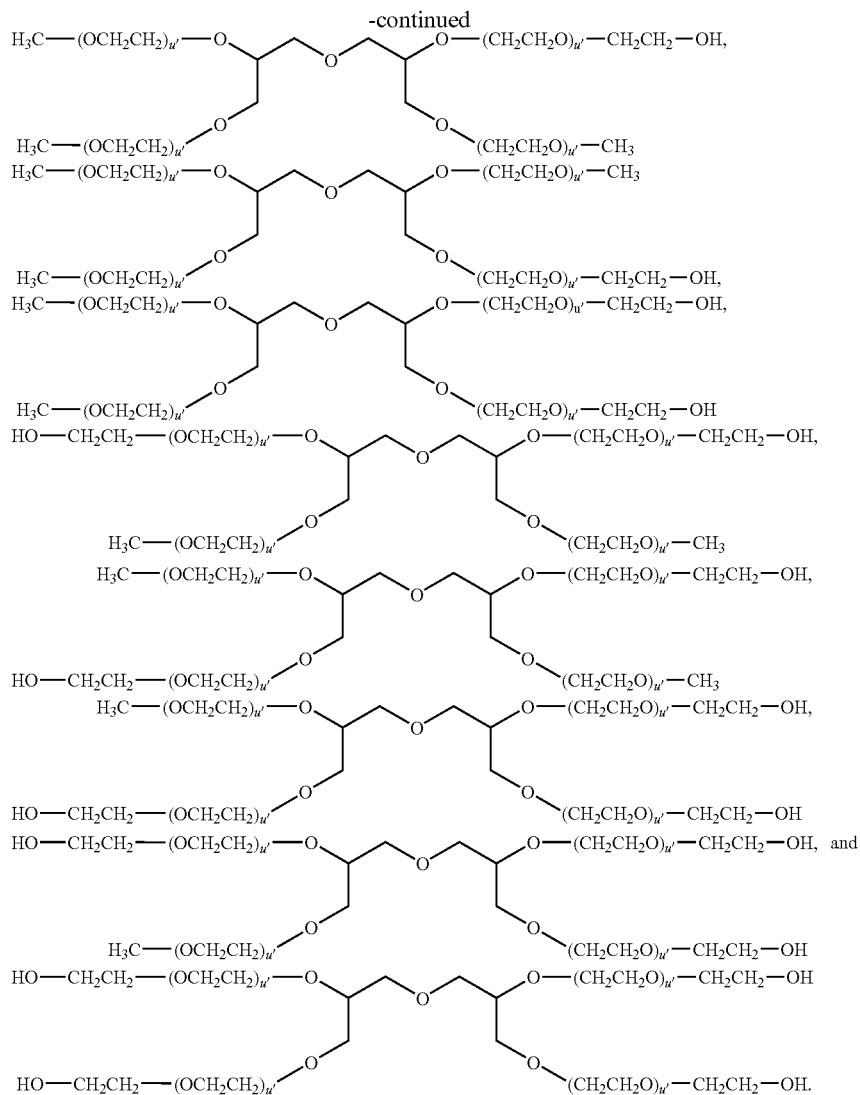

In a further embodiment, and as an alternative to PAO-based polymers, the substantially non-antigenic polymers are optionally selected from among one or more effectively non-antigenic materials such as dextran, polyvinyl alcohols, carbohydrate-based polymers, hydroxypropylmeth-acrylamide (HPMA), polyalkylene oxides, and/or copolymers thereof. See also commonly-assigned U.S. Pat. No. 6,153,655, the contents of which are incorporated herein by reference. It will be understood by those of ordinary skill that the same type of activation is employed as described herein as for PAO's such as PEG. Those of ordinary skill in the art will further realize that the foregoing list is merely illustrative and that all polymeric materials having the qualities described herein are contemplated.

For purposes of the present invention, "substantially or effectively non-antigenic" means all materials understood in the art as being nontoxic and not eliciting an appreciable immunogenic response in mammals.

Some preferred activated PEGs include PEG-amines used in combination with bifunctional spacers for attaching the polymer to the posaconazole, such as diglycolic acid or related spacers. In those aspects where linear, unbranched polymers are used, preferred embodiments include those in which the posaconazole is attached on both terminals (ends) of the polymer.

In further aspects, polymers having terminal amine groups can be employed to make the compounds described herein. The methods of preparing polymers containing terminal amines in high purity are described in U.S. patent application Ser. Nos. 11/508,507 and 11/537,172, the contents of each of which are incorporated by reference. For example, polymers having azides react with phosphine-based reducing agent such as triphenylphosphine or an alkali metal borohydride reducing agent such as $NaBH_4$. Alternatively, polymers including leaving groups react with protected amine salts such as potassium salt of methyl-tert-butyl imidodicarbonate (KNMeBoc) or the potassium salt of di-tert-butyl imidodicarbonate ($KNBoc_2$) followed by deprotecting the protected amine group. The purity of the polymers containing the terminal amines formed by these processes is greater than about 95% and preferably greater than 99%.

3. Preferred PEG-Posaconazole Conjugates

It has been surprisingly found that certain releasable polymer conjugates of posaconazole have increased potency as compared to unmodified versions thereof. The anti-fungal prodrugs of the present invention include those of Formula (I):

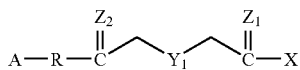

wherein

A is a capping group or

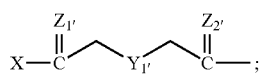

X is

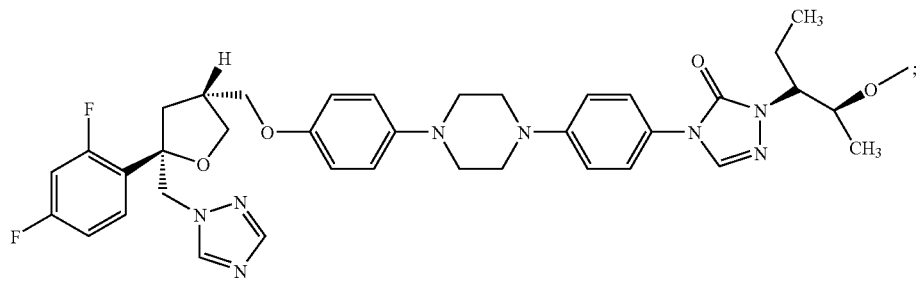

$Z_1$, $Z_{1'}$, $Z_2$ and $Z_{2'}$ are independently selected from among O, S and $NR_1$;

R is a polyalkylene oxide;

$Y_1$ and $Y_{1'}$ are independently O, S, SO, $SO_2$, $CR_2R_3$ or $NR_4$; and $R_1$, $R_2$, $R_3$ and $R_4$ are independently selected from among hydrogen, $C_{1-6}$ alkyls, $C_{3-19}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy.

In one aspect, A can be selected from among H, $NH_2$, OH, $CO_2H$, $C_{1-6}$ alkoxy, and $C_{1-6}$ alkyls. In some particular embodiments, A can be methyl, ethyl, methoxy, ethoxy, H, and OH. A is preferably methyl or methoxy.

In one preferred aspect, the polymeric conjugates of the invention have Formula (II):

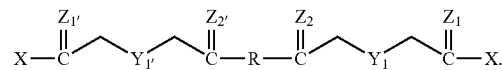

More preferably, the polymeric conjugates described herein have Formula (III):

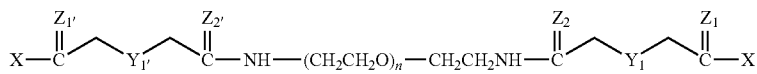

wherein (n) is an integer from about 20 to about 2300 so that the average molecular weight is from about 1,000 to about 100,000, preferably from about 5,000 to about 60,000 and more preferably from about 12,000 to about 24,000.

In particularly preferred aspects of the invention, $Y_1$, $Y_{1'}$, $Z_1$, $Z_{1'}$, $Z_2$ and $Z_{2'}$ are each O, (oxygen). Thus, some particularly preferred embodiments can have the structure:

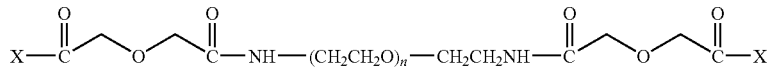

wherein X is
X is

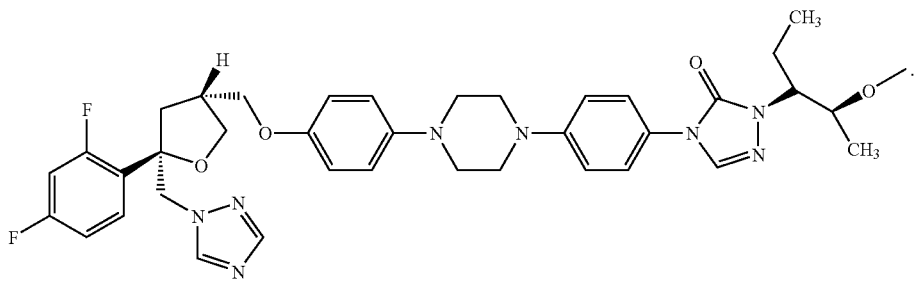

Some embodiments contemplated include mPEG instead of bis-PEG shown above. The polymeric conjugates can have the structure:

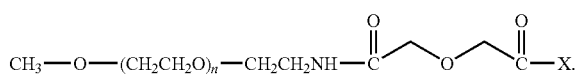

4. Methods of Synthesis

In another aspect of the invention, there are provided methods of preparing the polymeric prodrugs described herein. Preferably, the methods include (a) reacting a compound of the structure

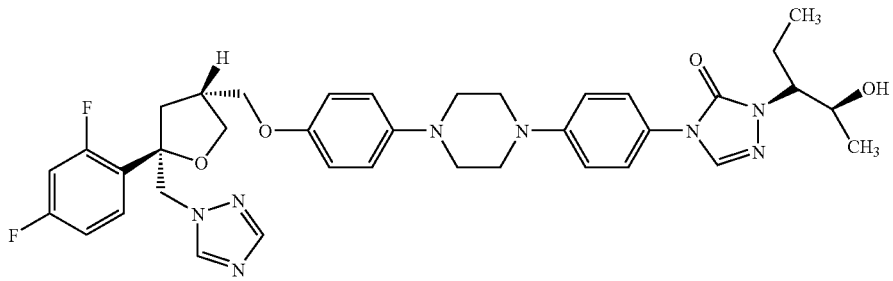

with a bifunctional spacer moiety such as

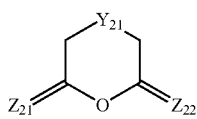

in the presence of a base
wherein
$Z_{21}$ and $Z_{22}$ are independently selected from among O, S and $NR_{21}$;

$Y_{21}$ is O, S, SO, $SO_2$, $CR_{22}R_{23}$ or $NR_{24}$; and $Y_{21}$, $R_{22}$, $R_{23}$ and $R_{24}$ are independently selected from among hydrogen, $C_{1-6}$ alkyls, $C_{3-19}$ branched alkyls, $C_{3-8}$ cycloalkyls, $C_{1-6}$ sub-stituted alkyls, $C_{3-8}$ substituted cycloalkyls, aryls, substituted aryls, aralkyls, $C_{1-6}$ heteroalkyls, substituted $C_{1-6}$ hetero-alkyls, $C_{1-6}$ alkoxy, phenoxy and $C_{1-6}$ heteroalkoxy; (preferably, $R_{22}$ and $R_{23}$ are both H (hydrogen)); and b) reacting the resulting product of step a) with an amine-terminated polyalkylene oxide of the formula:

$H_2N$—PAO—$NH_2$ (or PAO—$NH_2$) in the presence of a base and a coupling agent under conditions sufficient to form the conjugates of Formula (I).

In most embodiments, the amine-terminated PAO is a PEG containing an alpha and an omega terminal amine, sometimes referred to as PEG-$NH_2$. The PEG-$NH_2$ is available commercially from Nektar, for example, or can be synthesized from PEG diol using standard techniques. When the polymer is linear and contains amine at both terminals, posoconazole can be loaded doubly, compared to when the linear polymer contains amine only at one terminal (mPEG-$NH_2$). Multi-arm polymers can also be used for loading multiple loads of posaconazole. For example, NOF's 4 arm PEG can load up to 4 loads of posaconazole.

Generally, the polymeric conjugates of the invention are prepared by reacting one or more equivalents of the amine-terminated PAO with, for example, one or more equivalents per active site of posaconazole-bifunctional spacer intermediate under conditions which are sufficient to effectively cause the amino group to undergo a reaction with the carboxylic acid of the intermediate and form a linkage.

Alternatively, the polymeric conjugates described herein can be prepared by reacting the amine-terminated PAO with a bifunctional spacer such as diglycolic anhydride, followed by conjugating to posaconazole. In these aspects, diglycolic anhydride is preferably in high purity to allow sufficient percentage of pegylation.

As mentioned above, the reactions required to form the polymer conjugates are carried out in the presence of a base. Suitable bases include 4-dimethylaminopyridine (DMAP)-preferred, diisopropylethylamine, pyridine, triethylamine, KOH, potassium t-butoxide and NaOH etc.

The second step in the conjugate formation calls for the use of a coupling agent in addition to further amounts of base. A non-limiting list of suitable coupling agents include 1,3-diisopropyl-carbodiimide (DIPC), any suitable dialkyl carbodiimide, 2-halo-1-alkyl-pyridinium halides (Mukaiyama reagents), 1-(3-dimethylaminopropyl)-3-ethyl carbodiimide (EDC-preferred), propane phosphonic acid cyclic anhydride (PPACA) and phenyl dichlorophosphates, etc. which are available, for example from commercial sources such as Sigma-Aldrich Chemical, or synthesized using known techniques. EDC is a preferred coupling agent.

Preferably the substituents are reacted in an inert solvent such as tetrahydrofuran (THF), acetonitrile ($CH_3CN$), methylene chloride (DCM), chloroform ($CHCl_3$), dimethyl formamide (DMF) or mixtures thereof. The reactions are usually carried out at a temperature of from about 0° C. up to about 22° C. (room temperature).

It will be clear from the foregoing that other conjugation reactions involving activated polymers and the posaconazole can be carried out without undue experimentation.

or such organic acids as acetic: oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, tri-methylamine, histidine, procaine and the like.

Pharmaceutical compositions of this invention may contain in addition to an effective amount of a posaconazole or salt thereof inert pharmaceutically acceptable carriers and all necessary or desirable pharmaceutically acceptable excipients that may be included in the preferred intravenous or parenteral compositions. Parenteral forms to be injected intravenously, intramuscularly, or subcutaneously are usually in the form of a sterile solution, and may contain salts or glucose to make the solution isotonic.

6. Methods of Treatment

In broad aspects of the invention, there are provided at least thee (3) methods of treating mammals for conditions in which posaconazole is effective. A first embodiment includes methods of treating and/or preventing fungal infections in a mammal such as a human. The methods include administering to the mammal a therapeutically. i.e. anti-fungally effective amount of a polymeric conjugate described herein. A second embodiment of the invention includes methods of treating, reducing and/or preventing cancer or metastatie diseases in mammals. These methods include administering to the mammal an effective amount of a posaconazole polymer conjugate regardless of how made or described herein. In each of these embodiments, the methods include administering the posaconazole-containing conjugates parenterally. In yet a further embodiment, there are provided methods of treating, reducing and/or preventing cancer or metastatic diseases in a mammal by administering an effective amount of a compound of the formula:

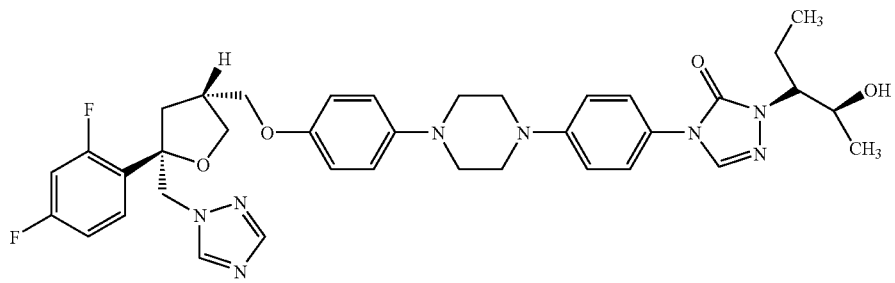

5. Pharmaceutical Compositions

A still further aspect of the invention includes pharmaceutical compositions containing an effective amount of the compounds or their pharmaceutically acceptable salts thereof described herein and a pharmaceutically acceptable carrier or excipient. The posaconazole described herein be formulated into a composition in a neutral or salt form. Pharmaceutically acceptable salts, include the acid addition salts (formed with the free amino groups of the protein). Some suitable inorganic acids include for example, hydrochloric or phosphoric acids, or a pharmaceuticatly acceptable salt thereof This aspect of the invention therefore embraces the use of posaconazole in compositions which are not necessarily part of polymer conjugates and thus can be administered in dosage forms via routes which are other than the parenteral, i.e. oral.

For purposes of the present invention, "treating or preventing cancer and/or metastatic diseases" shall be understood to mean that symptoms or conditions of the diseases are inhibited or attenuated during and/or after treatment when compared to that observed in the absence of the treatment described herein. The prevented conditions can be confirmed by biological or clinical markers contemplated by the artisan in the field.

Regardless of the methods of treatment employed, the amount of posaconazole administered to the patient in need thereof is from about 10 to about 2,000 mg per day, and is preferably from about 50 to about 800 mg per day. In alternative aspects, the amount administered is from about 5 to about 50 mg/kg/day. The administration can be made as part of a single daily dose or multiple doses given daily. In all aspects of the invention where polymeric conjugates are administered, the dosage amount mentioned is based on the amount of posaconazole rather than the amount of polymeric conjugate administered. It is contemplated that the treatment will be given for one or more days until the desired clinical result is obtained. For example, in those aspects of the invention where the polymeric conjugates are administered for the purpose of treating fungal disease, the amount of posaconazole administered to the patient in need thereof is an amount effective to produce an arithmetic mean steady state average maximum plasma concentration of posaconazole that exceeds the majority of the Minimum Inhibitory Concentrations needed to kill 50%, preferably 80%, more preferably 90% ("MICs$_{90}$") of the clinically relevant pathogenic fungi.

The methods contemplated herein also include administering the posaconazole or polymeric conjugates described herein one or more times (i.e. twice) weekly for one or more weeks until such time as conditions of cancer and metastatic diseases are abated. The compositions may be administered once daily or divided into multiple doses which can be given as part of a multi-week treatment protocol.

The exact amount, frequency and period of administration of the compound of the present invention will vary, of course, depending upon the sex, age and medical condition of the patent as well as the severity of the antifungal infection, cancer or metastatic diseases as determined by the attending clinician.

Still further aspects include combining the posaconazole compositions described herein with other antifungals or anticancer therapies for synergistic or additive benefit. For example, the posaconazole and polymeric conjugates according to the methods described herein can be used in combination, simultaneously or sequentially, with a chemotherapeutic agent treatment.

EXAMPLES

The following examples serve to provide further appreciation of the invention but are not meant in any way to restrict the effective scope of the invention. The bold-faced numbers recited in the Examples correspond to those shown in FIG. 1.

Example 1

Compound 1 (5.0 g, 7.135 mmol), 4-(dimethylamino)pyridinen (DMAP) (3.49 g, 28.5 mmol), diglycolic anhydride (1.66 g, 14.3 mmol) were dissolved in 200 mL anhydrous methylene chloride and stirred for 2 hours. The solution was then washed by 4×100 mL 0.1 N HCl and dried by MgSO$_4$. The solution was filtered, evaporated, and dried over P$_2$O$_5$ under vacuum overnight to give pure compound 2 (5.61 g, 6.87 mmol, 96%). $^{13}$C NMR (67.8 MHz, CDCl$_3$) δ 10.23, 17.11, 22.07, 37.33, 38.65, 48.73, 50.69, 53.34, 55.88, 60.18, 68.03, 68.18, 68.75, 70.53, 71.96, 83.76 (J$_{CF}$=4 Hz), 104.46 (J$_{CF}$=26 Hz), 111.18 (J$_{CF}$=20 Hz), 115.03, 116.51, 118.66, 123.53, 125.11 (J$_{CF}$=12 Hz), 125.39, 128.44 (J$_{CF}$=7 Hz), 134.64, 144.32, 144.81, 150.21, 150.32, 153.03, 153.32, 158.78 (J$_{CF}$=244 Hz, J$_{CF}$=12 Hz), 162.59 (J$_{CF}$=248 Hz, J$_{CF}$=12 Hz), 169.07, 171.42.

Example 2

ΔPEG 20 k Da amine (bis-PEG-amine) 3 (40 g, 2.0 mmol) was dried by azeotrope with 300 mL toluene and the solvent was evaporated to give a solid. It was then dissolved in 400 mL anhydrous methylene chloride together with 2 (5.88 g, 7.19 mmol) and DMAP (3.91 g, 32.0 mmol). The solution was chilled to 0° C. by an ice-bath for 20 minutes, then 1-[3-(dimethylamino)propyl]-3-ethylcarbodiimide hydrochloride (EDC) (3.07 g, 16.0 mmol) was added. The reaction mixture was allowed to warm to room temperature and was stirred overnight. It was then evaporated to solid and first recrystallized from 900 mL IA, then recrystallized from 450 mL THF to give pure compound 4 (40.1 g, 1.86 mmol, 93%). $^{13}$C NMR (67.8 MHz, CDCl$_3$) δ9.47, 16.31, 21.13, 36.36, 37.56, 37.87, 48.03, 49.48, 54.73, 59.16, 82.95 (J$_{CF}$=4 Hz), 103.60 (J$_{CF}$=26 Hz) 110.27 (J$_{CF}$=21 Hz, J$_{CF}$=2 Hz), 114.09, 415.36, 117.27, 122.38, 124.70, 124.82 (J$_{CF}$=2 Hz), 127.57 (J$_{CF}$=9 Hz), 134.10, 143.78, 144.73, 149.44, 149.90, 151.89, 152.02, 158.06 (J$_{CF}$=247 Hz, J$_{CF}$=12 Hz) 161.62 (J$_{CF}$=253 Hz, J$_{CF}$=11 Hz), 167.72, 167.79.

Example 3

In this example various in vivo and in vitro tests were conducted. The results are provided below.

| compound | MW | $t_{1/2}$ (h) (pH = 7.4 buffer) | $t_{1/2}$ (h) (in vitro, rat plasma) | $t_{1/2}$ (h) (in vivo, mice) | Solubility in water (mg/mL) | equivalency to Posaconazole (mg/mL) |
|---|---|---|---|---|---|---|
| 4 | 20,000 | 14.4 | 0.87 | 0.6 | 102 | 6.6 |

What is claimed is:

1. A polymeric conjugate having Formula (III):

$$X-\overset{Z_{1'}}{\underset{\|}{C}}-CH_2-Y_{1'}-CH_2-\overset{Z_{2'}}{\underset{\|}{C}}-NH-(CH_2CH_2O)_n-$$

$$-CH_2CH_2NH-\overset{Z_2}{\underset{\|}{C}}-CH_2-Y_1-CH_2-\overset{Z_1}{\underset{\|}{C}}-X$$

wherein

X is

[structure of posaconazole-derived moiety]

$Z_1$, $Z_{1'}$, $Z_2$ and $Z_{2'}$ are O;

$Y_1$ and $Y_{1'}$ are O; and (n) is a positive integer so that the polyethylene glycol has a weight average molecular weight of about 20,000 daltons.

2. A method of preparing a polymeric conjugate of claim 1, comprising a) reacting a compound of the structure

[posaconazole structure]

with

[structure with $Y_{21}$, $Z_{21}$, $Z_{22}$]

in the presence of a base wherein $Z_{21}$ and $Z_{22}$ are O;

$Y_{21}$ is O, and b) reacting the resulting product of step a) with an amine-terminated polyalkylene oxide in the presence of a base and a coupling agent under conditions sufficient to form a polymeric conjugate of claim 1.

3. The method of claim 1, wherein the base is 4-dimethylaminopyridine (DMAP) and the coupling agent is 1-[3-(dimethylamino)propyl]-3-ethylcarbodiimide hydrochloride (EDC).

4. A pharmaceutical composition comprising an effective amount of the polymeric conjugate of claim 1 or a pharmaceutically acceptable salt thereof and a pharmaceutically acceptable carrier.

5. A method of treating or preventing fungal infections in a mammal, comprising administering an anti-fungally effective amount of a polymeric conjugate of claim 1 to a mammal in need thereof.

6. The method of claim 5, wherein the polymeric conjugate is administered parenterally.

7. The method of claim 5, wherein the amount of posaconazole administered to the mammal is from about 10 to about 2,000 mg per day.

8. The method of claim 5, wherein the amount of posaconazole administered to the mammal is from about 50 to about 800 mg per day.

9. The method of claim 5, wherein the amount of posaconazole administered to the mammal is from about 5 to about 50 mg/kg/day.

10. The method of claim 5, wherein the amount of posaconazole administered is an amount effective to produce an arithmetic mean steady state average maximum plasma concentration of posaconazole that exceeds the majority of the Minimum Inhibitory Concentrations needed to kill 90% ("MICs$_{90}$") of the clinically relevant pathogenic fungi.

* * * * *